(12) United States Patent
Jung

(10) Patent No.: US 8,919,341 B2
(45) Date of Patent: Dec. 30, 2014

(54) INHALER

(75) Inventor: Andree Jung, Ingelheim am Rhein (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 717 days.

(21) Appl. No.: 13/130,131

(22) PCT Filed: Nov. 27, 2009

(86) PCT No.: PCT/EP2009/065949
§ 371 (c)(1),
(2), (4) Date: Jul. 20, 2011

(87) PCT Pub. No.: WO2010/063645
PCT Pub. Date: Jun. 10, 2010

(65) Prior Publication Data
US 2011/0297151 A1 Dec. 8, 2011

(30) Foreign Application Priority Data

Dec. 3, 2008 (EP) .................................. 08170606

(51) Int. Cl.
| A62B 7/00 | (2006.01) |
| A61M 15/00 | (2006.01) |
| A61M 16/00 | (2006.01) |
| A61M 11/00 | (2006.01) |

(52) U.S. Cl.
CPC ....... *A61M 15/0045* (2013.01); *A61M 15/0003* (2014.02); *A61M 15/0043* (2014.02); *A61M 15/0021* (2014.02); *A61M 11/002* (2014.02); *A61M 2202/064* (2013.01); *A61M 15/0048* (2014.02)
USPC ............. 128/203.15; 128/200.24; 128/203.12

(58) Field of Classification Search
None
See application file for complete search history.

(56) References Cited

U.S. PATENT DOCUMENTS

| 4,627,432 A | * | 12/1986 | Newell et al. ............. | 128/203.15 |
| 5,207,217 A | * | 5/1993 | Cocozza et al. ......... | 128/203.21 |
| 5,301,666 A | * | 4/1994 | Lerk et al. ................ | 128/203.15 |
| 5,642,727 A | * | 7/1997 | Datta et al. ............... | 128/203.15 |

(Continued)

FOREIGN PATENT DOCUMENTS

| CA | 2644263 A1 | 10/2007 |
| EP | 1844806 A1 | 10/2007 |

(Continued)

OTHER PUBLICATIONS

International Search Report, Form PCT/ISA/210, for corresponding PCT/EP2009/065949; date of mailing: Mar. 3, 2010.

*Primary Examiner* — Tan-Uyen Jackie T Ho
*Assistant Examiner* — Eric Bryant
(74) *Attorney, Agent, or Firm* — Michael P. Morris; Mary-Ellen M. Devlin

(57) ABSTRACT

An inhaler, particularly a powder inhaler, for administering a medicament in the form of inhalable substances, substance formulations or mixtures, with a mouthpiece (2) and a magazine that comprises a housing (3) having a plurality of cavities (32) for holding the medicament, the mouthpiece (2) being in flow connection with one of the cavities (32). The closed housing (3) has a cover (4) that covers at least one carrier (26, 27) comprising the unsealed cavities (32), the carrier (26, 27) being movable relative to the cover (4) for bringing a cavity (32) into flow connection with the mouthpiece (2).

16 Claims, 4 Drawing Sheets

(56) References Cited

U.S. PATENT DOCUMENTS

| | | | | |
|---|---|---|---|---|
| 5,809,997 A * | 9/1998 | Wolf | ................... | 128/200.23 |
| 6,116,238 A * | 9/2000 | Jackson et al. | ........... | 128/203.15 |
| 6,948,492 B2 * | 9/2005 | Wermeling et al. | ...... | 128/200.14 |
| 2002/0048552 A1 * | 4/2002 | Garrill et al. | ............ | 424/45 |
| 2003/0140923 A1 * | 7/2003 | Taylor et al. | ............. | 128/203.12 |
| 2006/0196504 A1 * | 9/2006 | Augustyn et al. | ........ | 128/203.15 |
| 2007/0181123 A1 | 8/2007 | Houzego | | |
| 2007/0235029 A1 * | 10/2007 | Zhu et al. | .................. | 128/203.12 |
| 2009/0114220 A1 | 5/2009 | Wachtel et al. | | |
| 2011/0297151 A1 | 12/2011 | Jung | | |

FOREIGN PATENT DOCUMENTS

| | | |
|---|---|---|
| JP | 2001524363 A | 12/2001 |
| JP | 2003535655 A | 12/2003 |
| JP | 2006518658 A | 8/2006 |
| WO | 9528192 A1 | 10/1995 |
| WO | 9927987 A1 | 6/1999 |
| WO | 9936116 A1 | 7/1999 |
| WO | 0045879 A1 | 8/2000 |
| WO | 0197886 A1 | 12/2001 |
| WO | 2005016424 A2 | 2/2005 |
| WO | 2010063645 A1 | 6/2010 |

* cited by examiner

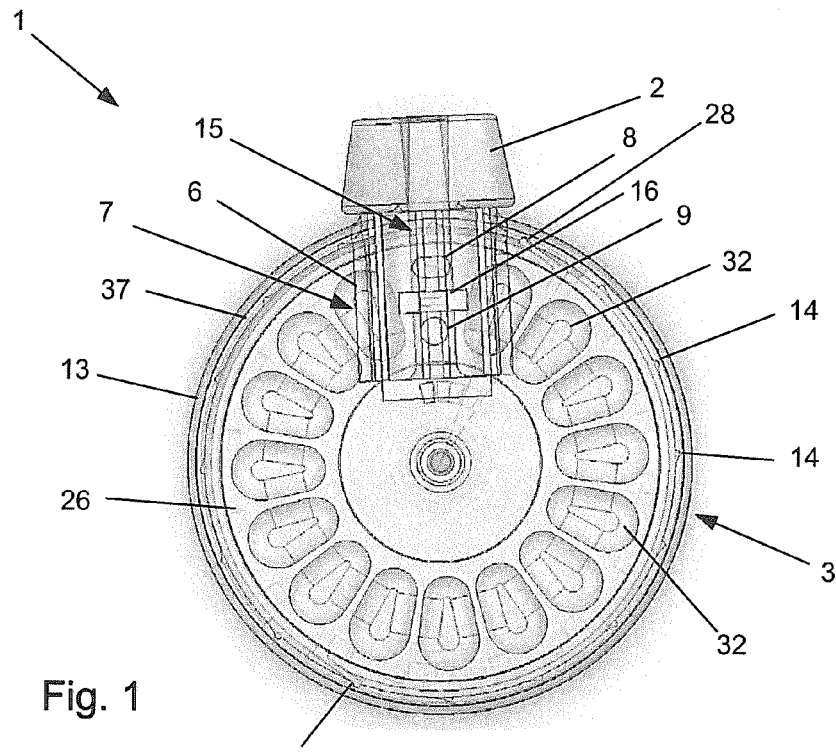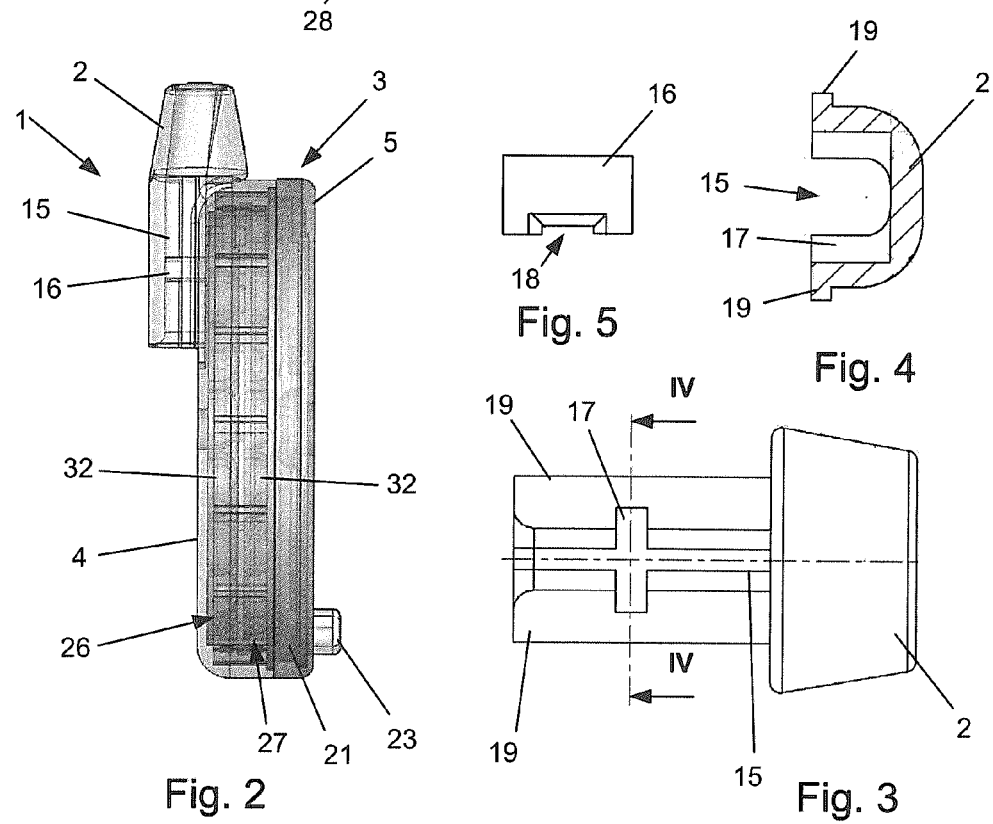

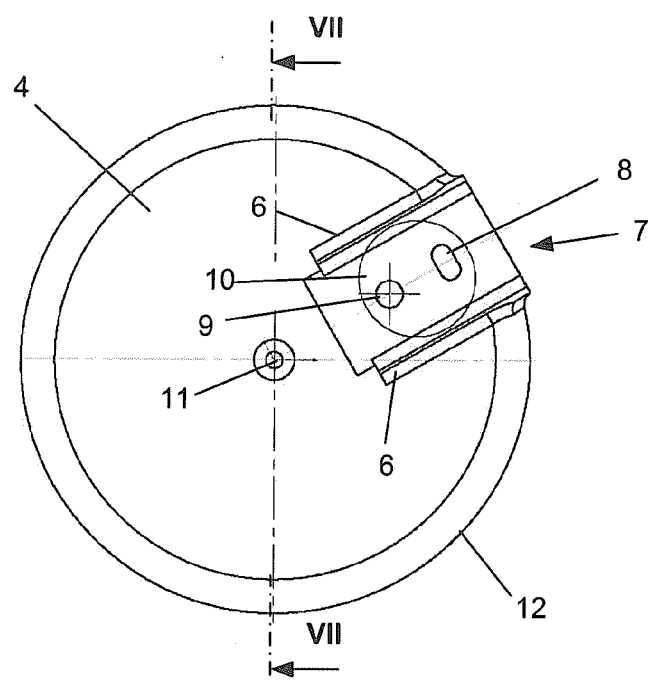
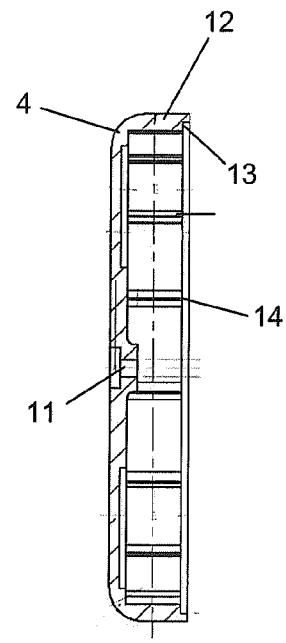
Fig. 6          Fig. 7
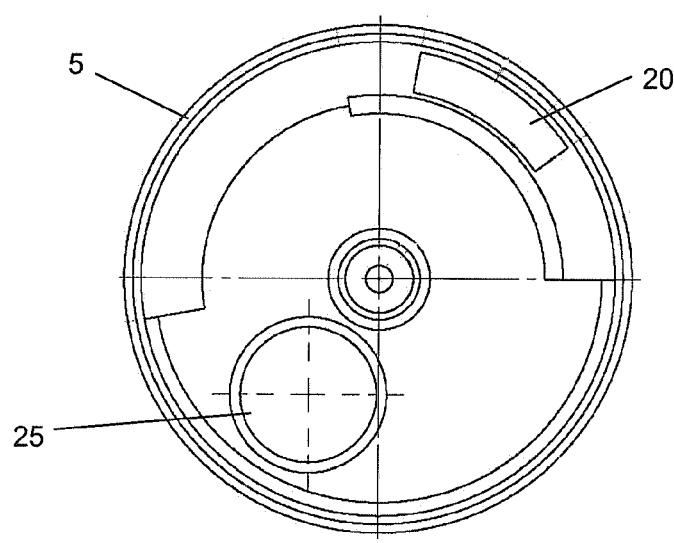
Fig. 8

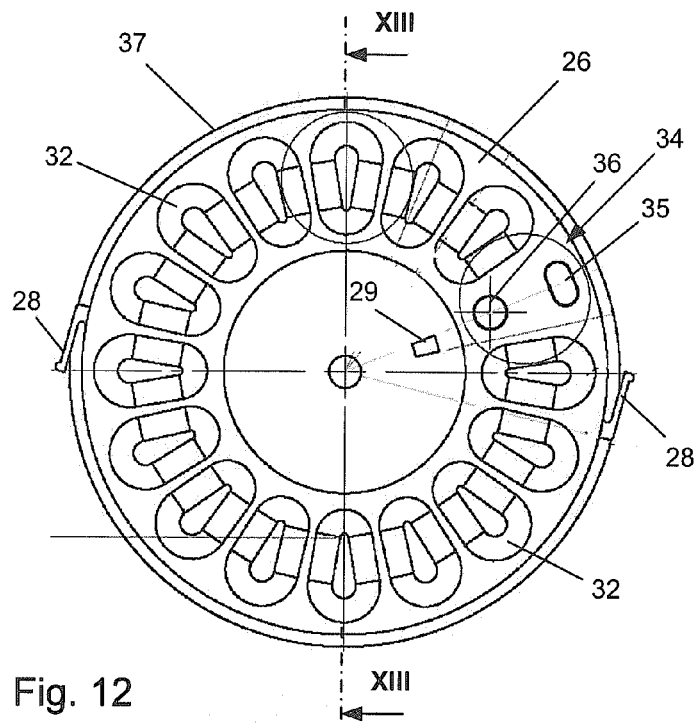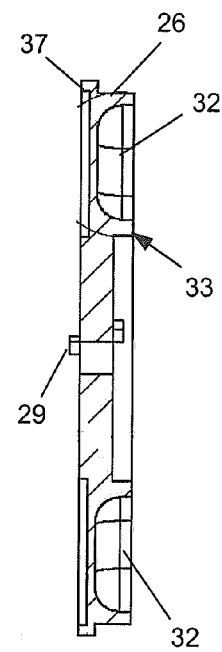
Fig. 12    Fig. 13
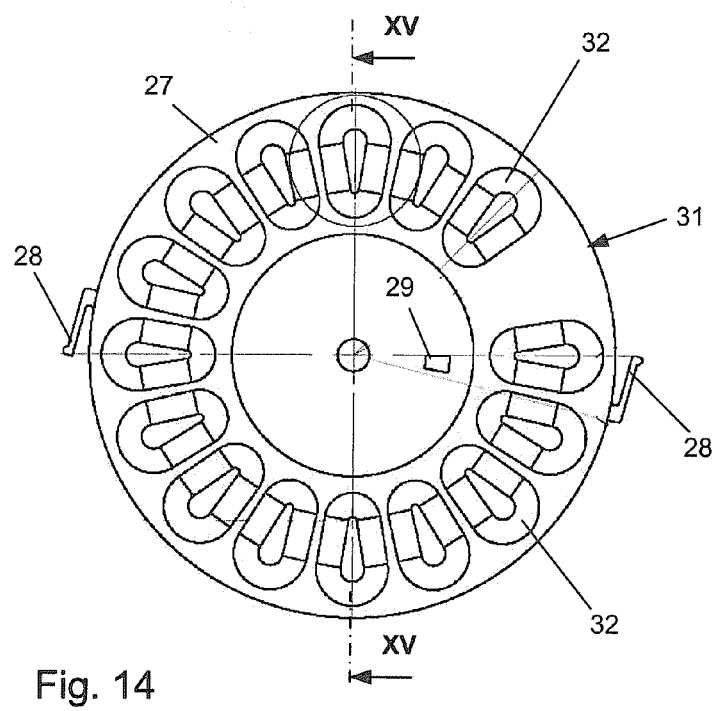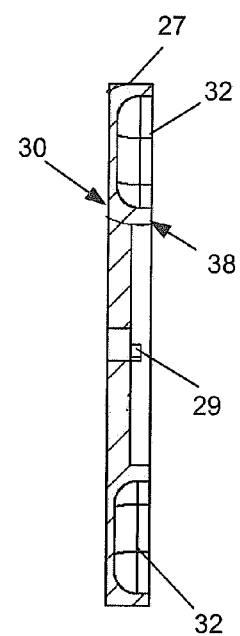
Fig. 14    Fig. 15

INHALER

The invention relates to an inhaler, particularly a powder inhaler, for administering a medicament in the form of inhalable substances, substance formulations or mixtures, with a mouthpiece and a magazine that comprises a housing having a plurality of cavities for holding the medicament, the mouthpiece being in flow connection with one of the cavities.

Inhalers are known from the prior art in which a direct connection is made to a medicament chamber by a reduced-pressure flow produced on inhaling (venturi) and a powdered medicament contained therein is removed. In an inhaler according to US-A-6 655 381 a powdered medicament is stored in an annular magazine in cavities arranged in a circle. A seal that closes off the cavities is essentially removed as a whole and a venturi tube with a constriction is arranged above the cavity parallel to the magazine. A longer turbulence chamber is connected to the venturi tube for removing the medicament from the cavity essentially in one go.

In addition, there are inhalers in which a medicament chamber is opened by piercing. The openings thus formed in a sealing film are not very precisely defined, however.

Moreover, EP 1 844 806 A1 describes a multi-dose powder inhaler in which a drive flow is produced in an air channel and because of a constriction in the air channel produces a reduced-pressure flow in this region. The narrowest part of the air channel causing the reduced-pressure flow is connected to a discharge opening of a medicament chamber. The discharge opening is connected to a control opening, so that a discharge flow is formed through the control opening via the discharge opening and through the medicament chamber. The discharge flow is not connected to the drive flow before entering the medicament chamber, but combines with the drive flow after exiting the discharge opening, as a result of which a medicament that has been carried along with the discharge flow is transported back towards the mouthpiece with the drive flow. The medicament magazine typically comprises, in addition to the control and discharge openings, a fill opening which is provided independently of the other two openings in the magazine and which may be relatively large to make filling easier. After being filled with the powder the fill opening is sealed with a film. If the medicament magazine is configured as an annular magazine with a plurality of medicament chambers arranged in a circle therein, the control and discharge opening of each chamber are spaced from one another on one side of the magazine, while the fill opening is arranged on an opposite side of the magazine.

The problem of the invention is to provide an inhaler of the kind mentioned hereinbefore, which is easy and reliable to operate while having a simple structure.

According to the invention the problem is solved in that the closed housing has a cover that covers at least one carrier comprising the unsealed cavities, the carrier being movable relative to the cover for bringing a cavity into flow connection with the mouthpiece.

In order to use the inhaler, which is constructed in particular as a so-called multi-dose powder inhaler, it is not necessary to remove a seal from the cavities or to pierce such a seal. Rather, the cavities containing the medicament are covered only by the cover of the housing. The invention is based on the finding that it is not absolutely essential to protect the medicament in the cavities from moisture by sealing with special films if the medicament is to be taken regularly and the magazine provides only as many doses of medicament as are normally consumed over the life of the medicament when it is correctly stored.

Inhalers are known by the trade marks HandiHaler®, Spinhaler®, Rotahaler®, Aerolizer®, Flowcaps®, Turbospin®, AIR DPI®, Orbital®, Directhaler® and/or are described in DE 33 45 722, EP 0 591 136, DE 43 18 455, WO 91/02558, FR-A-2 146 202, U.S. Pat. No. 4,069,819, EP 666085, EP 869079, U.S. Pat. No. 3,991,761, WO 99/45987, WO 200051672, Bell, J. Pharm. Sci. 60, 1559 (1971); Cox, Brit. Med. J. 2, 634 (1969). Both single- and multi-dose powder inhalers are known, particularly the Spinhaler®, Rotahaler®, Aerolizer®, Inhalator®, HandiHaler®, Diskhaler®, Diskus®, Accuhaler®, Aerohaler®, Eclipse®, Turbohaler®, Turbuhaler®, Easyhaler®, Novolizer®, Clickhaler®, Pulvinal®, Novolizer®, SkyeHaler®, Xcelovair®, Pulvina®, Taifun®, MAGhaler®, Twisthaler® and Jethaler®.

Particularly preferred in this context are medicaments selected from among the anticholinergics, betamimetics, steroids, phosphodiesterase IV inhibitors, LTD4-antagonists and EGFR-kinase inhibitors, antiallergics, ergot alkaloid derivatives, triptanes, CGRP antagonists, phosphodiesterase-V inhibitors, and combinations of active substances of this kind, e.g. betamimetics plus anticholinergics or betamimetics plus antiallergics. In the case of combinations at least one of the active substances contains chemically bound water. Anticholinergic-containing active substances are preferably used, as monopreparations or in the form of combined preparations.

The following are specific examples of the active ingredients or the salts thereof:

Anticholinergics to be used are preferably selected from among tiotropium bromide, oxitropium bromide, flutropium bromide, ipratropium bromide, glycopyrronium salts, trospium chloride, tolterodine, tropenol 2,2-diphenylpropionate methobromide, scopine 2,2-diphenylpropionate methobromide, scopine 2-fluoro-2,2-diphenylacetate-methobromide, tropenol 2-fluoro-2,2-diphenylacetate-methobromide, tropenol 3,3',4,4'-tetrafluorobenzilate methobromide, scopine 3,3', 4,4'-tetrafluorobenzilate methobromide, tropenol 4,4'-difluorobenzilate methobromide, scopine 4,4'-difluorobenzilate methobromide, tropenol 3,3'-difluorobenzilate methobromide, scopine 3,3'-difluorobenzilate methobromide, tropenol 9-hydroxy-fluorene-9-carboxylate methobromide, tropenol 9-fluoro-fluorene-9-carboxylate methobromide, scopine 9-hydroxy-fluorene-9-carboxylate methobromide, scopine 9-fluoro-fluorene-9-carboxylate methobromide, tropenol 9-methyl-fluorene-9-carboxylate methobromide, scopine 9-methyl-fluorene-9-carboxylate methobromide, cyclopropyltropine benzilate methobromide, 2,2-diphenylpropionate cyclopropyltropine methobromide, cyclopropyltropine 9-hydroxy-xanthene-9-carboxylate methobromide, cyclopropyltropine benzilate methobromide, 2,2-diphenylpropionate cyclopropyltropine methobromide, cyclopropyltropine 9-hydroxy-xanthene-9-carboxylate methobromide, cyclopropyltropine 9-methyl-fluorene-9-carboxylate methobromide, cyclopropyltropine 9-methyl-xanthene-9-carboxylate methobromide, cyclopropyltropine 9-hydroxy-fluorene-9-carboxylate methobromide, methyl cyclopropyltropine 4,4'-difluorobenzilate methobromide, tropenol 9-hydroxy-xanthene-9-carboxylate methobromide, scopine 9-hydroxy-xanthene-9-carboxylate methobromide, tropenol 9-methyl-xanthene-9-carboxylate methobromide, scopine 9-methyl-xanthene-9-carboxylate methobromide, tropenol 9-ethyl-xanthene-9-carboxylate methobromide, tropenol 9-difluoromethyl-xanthene-9-carboxylate methobromide and scopine 9-hydroxymethyl-xanthene-9-carboxylate methobromide, optionally in the form of the racemates, enantiomers or diastereomers thereof and optionally in the form of the salts, solvates and/or hydrates thereof.

Betamimetics which may be used are preferably selected from among albuterol, bambuterol, bitolterol, broxaterol, carbuterol, clenbuterol, fenoterol, formoterol, hexoprenaline, ibuterol, indacterol, isoetharine, isoprenaline, levosalbutamol, mabuterol, meluadrine, metaproterenol, orciprenaline, pirbuterol, procaterol, reproterol, rimiterol, ritodrine, salmeterol, salmefamol, soterenot, sulphonterol, tiaramide, terbutaline, tolubuterol, CHF-1035, HOKU-81, KUL-1248, 3-(4-{6-[2-hydroxy-2-(4-hydroxy-3-hydroxymethyl-phenyl)-ethylamino]-hexyloxy}-butyl)-benzenesulphonamide, 5-[2-(5,6-diethyl-indan-2-ylamino)-1-hydroxy-ethyl]-8-hydroxy-1H-quinolin-2-one, 4-hydroxy-7-[2-{[2-{[3-(2-phenylethoxy)propyl]sulphonyl}ethyl]-amino}ethyl]-2(3H)-benzothiazolone, 1-(2-fluoro-4-hydroxyphenyl)-2-[4-(1-benzimidazolyl)-2-methyl-2-butylamino]ethanol, 1-[3-(4-methoxybenzyl-amino)-4-hydroxyphenyl]-2-[4-(1-benzimidazolyl)-2-methyl-2-butylamino]ethanol, 1-[2H-5-hydroxy-3-oxo-4H-1,4-benzoxazin-8-yl]-2-[3-(4-N,N-dimethylaminophenyl)-2-methyl-2-propylamino]ethanol, 1-[2H-5-hydroxy-3-oxo-4H-1,4-benzoxazin-8-yl]-2-[3-(4-methoxyphenyl)-2-methyl-2-propylamino]ethanol, 1-[2H-5-hydroxy-3-oxo-4H-1,4-benzoxazin-8-yl]-2-[3-(4-n-butyloxyphenyl)-2-methyl-2-propylamino]ethanol, 1-[2H-5-hydroxy-3-oxo-4H-1,4-benzoxazin-8-yl]-2-{4-[3-(4-methoxyphenyl)-1,2,4-triazol-3-yl]-2-methyl-2-butylamino}ethanol, 5-hydroxy-8-(1-hydroxy-2-isopropylaminobutyl)-2H-1,4-benzoxazin-3-(4H)-one, 1-(4-amino-3-chloro-5-trifluoromethylphenyl)-2-tert.-butylamino)ethanol and 1-(4-ethoxycarbonylamino-3-cyano-5-fluorophenyl)-2-(tert.-butylamino)ethanol, optionally in the form of the racemates, enantiomers or diastereomers thereof and optionally in the form of the pharmacologically acceptable acid addition salts, solvates and/or hydrates thereof.

Steroids which may be used are preferably selected from among prednisolone, prednisone, butixocortpropionate, RPR-106541, flunisolide, beclomethasone, triamcinolone, budesonide, fluticasone, mometasone, ciclesonide, rofleponide, ST-126, dexamethasone, (S)-fluoromethyl 6α, 9α-difluoro-17α-[(2-furanylcarbonyl)oxy]-11β-hydroxy-16α-methyl-3-oxo-androsta-1,4-diene-17β-carbothionate, (S)-(2-oxo-tetrahydro-furan-3S-yl) 6α,9α-difluoro-11β-hydroxy-16α-methyl-3-oxo-17α-propionyloxy-androsta-1,4-diene-17β-carbothionate and etiprednol-dichloroacetate (BNP-166), optionally in the form of the racemates, enantiomers or diastereomers thereof and optionally in the form of the salts and derivatives thereof, the solvates and/or hydrates thereof.

PDE IV inhibitors which may be used are preferably selected from among enprofyllin, theophyllin, roflumilast, ariflo (cilomilast), CP-325,366, BY343, D-4396 (Sch-351591), AWD-12-281 (GW-842470), N-(3,5-dichloro-1-oxo-pyridin-4-yl)-4-difluoromethoxy-3-cyclopropylmethoxybenzamide, NCS-613, pumafentine, (−)p-[(4aR*,10bS*)-9-ethoxy-1,2,3,4,4a,10b-hexahydro-8-methoxy-2-methylbenzo[s][1,6]naphthyridin-6-yl]-N,N-diisopropylbenzamide, (R)-(+)-1-(4-bromobenzyl)-4-[(3-cyclopentyloxy)-4-methoxyphenyl]-2-pyrrolidone, 3-(cyclopentyloxy-4-methoxyphenyl)-1-(4-N'-[N-2-cyano-S-methyl-isothioureido]benzyl)-2-pyrrolidone, cis[4-cyano-4-(3-cyclopentyloxy-4-methoxyphenyl)cyclohexane-1-carboxylic acid], 2-carbomethoxy-4-cyano-4-(3-cyclopropylmethoxy-4-difluoromethoxyphenyl)cyclohexan-1-one, cis[4-cyano-4-(3-cyclopropylmethoxy-4-difluoromethoxyphenyl)cyclohexan-1-ol], (R)-(+)-ethyl[4-(3-cyclopentyloxy-4-methoxyphenyl)pyrrolidin-2-ylidene]acetate, (S)-(−)-ethyl[4-(3-cyclopentyloxy-4-methoxyphenyl)pyrrolidin-2-ylidene]acetate, CDP840, Bay-198004, D-4418, PD-168787, T-440, T-2585, arofyllin, atizoram, V-11294A, C1-1018, CDC-801, CDC-3052, D-22888, YM-58997, Z-15370, 9-cyclopentyl-5,6-dihydro-7-ethyl-3-(2-thienyl)-9H-pyrazolo[3,4-c]-1,2,4-triazolo[4,3-a]pyridine and 9-cyclopentyl-5,6-dihydro-7-ethyl-3-(tert-butyl)-9H-pyrazolo[3,4-c]-1,2,4-triazolo[4,3-a]pyridine, optionally in the form of the racemates, enantiomers or diastereomers thereof and optionally in the form of the pharmacologically acceptable acid addition salts, solvates and/or hydrates thereof.

LTD4-antagonists which may be used are preferably selected from among montelukast, 1-(((R)-(3-(2-(6,7-difluoro-2-quinolinyl)ethenyl)phenyl)-3-(2-(2-hydroxy-2-propyl)phenyl)thio)methylcyclopropane-acetic acid, 1-(((1(R)-3(3-(2-(2,3-dichlorothieno[3,2-b]pyridin-5-yl)-(E)-ethenyl)phenyl)-3-(2-(1-hydroxy-1-methylethyl)phenyl)propyl)thio)-methyl)cyclopropane-acetic acid, pranlukast, zafirlukast, [2-[[2-(4-tert-butyl-2-thiazolyl)-5-benzofuranyl]oxymethyl]phenyl]acetic acid, MCC-847 (ZD-3523), MN-001, MEN-91507 (LM-1507), VUF-5078, VUF-K-8707 and L-733321, optionally in the form of the racemates, enantiomers or diastereomers thereof, optionally in the form of the pharmacologically acceptable acid addition salts thereof and optionally in the form of the salts and derivatives thereof, the solvates and/or hydrates thereof.

EGFR-kinase inhibitors which may be used are preferably selected from among cetuximab, trastuzumab, ABX-EGF, Mab ICR-62, 4-[(3-chloro-4-fluorophenyl)amino]-6-{[4-(morpholin-4-yl)-1-oxo-2-buten-1-yl]amino}-7-cyclopropylmethoxy-quinazoline, 4-[(R)-(1-phenyl-ethyl)amino]-6-{[4-(morpholin-4-yl)-1-oxo-2-buten-1-yl]amino}-7-cyclopentyloxy-quinazoline, 4-[(3-chloro-4-fluoro-phenyl)amino]-6-{[4-((R)-6-methyl-2-oxo-morpholin-4-yl)-1-oxo-2-buten-1-yl]amino}-7-[(S)-(tetrahydrofuran-3-yl)oxy]-quinazoline, 4-[(3-chloro-4-fluoro-phenyl)amino]-6-[2-((S)-6-methyl-2-oxo-morpholin-4-yl)-ethoxy]-7-methoxy-quinazoline, 4-[(3-chloro-4-fluorophenyl)amino]-6-({4-[N-(2-methoxy-ethyl)-N-methyl-amino]-1-oxo-2-buten-1-yl}amino)-7-cyclopropylmethoxy-quinazoline, 4-[(R)-(1-phenyl-ethyl)amino]-6-({4[N-(tetrahydropyran-4-yl)-N-methyl-amino]-1-oxo-2-buten-1-yl}amino)-7-cyclopropylmethoxy-quinazoline, 4-[(3-chloro-4-fluorophenyl)amino]-6-({4[N-(2-methoxy-ethyl)-N-methyl-amino]-1-oxo-2-buten-1-yl}amino)-7-cyclopentyloxy-quinazoline, 4-[(3-chloro-4-fluorophenyl)amino]-6-{[4-(N,N-dimethylamino)-1-oxo-2-buten-1-yl]amino}-7-[(R)-(tetrahydrofuran-2-yl)methoxy]-quinazoline, 4-[(3-ethynyl-phenyl)amino]-6,7-bis-(2-methoxy-ethoxy)-quinazoline, 4-[(R)-(1-phenyl-ethyl)amino]-6-(4-hydroxy-phenyl)-7H-pyrrolo[2,3-d]pyrimidine, 3-cyano-4-[(3-chloro-4-fluorophenyl)amino]-6-{[4-(N,N-dimethylamino)-1-oxo-2-buten-1-yl]amino}-7-ethoxy-quinoline, 4-[(R)-(1-phenyl-ethyl)amino]-6-{[4-((R)-6-methyl-2-oxo-morpholin-4-yl)-1-oxo-2-buten-1-yl]amino}-7-methoxy-quinazoline, 4-[(3-chloro-4-fluorophenyl)amino]-6-{[4-(morpholin-4-yl)-1-oxo-2-buten-1-yl]amino}-7-[(tetrahydrofuran-2-yl)methoxy]-quinazoline, 4-[(3-ethynyl-phenyl)amino]-6-{[4-(5,5-dimethyl-2-oxo-morpholin-4-yl)-1-oxo-2-buten-1-yl]amino}-quinazoline, 4-[(3-chloro-4-fluoro-phenyl)amino]-6-{2-[4-(2-oxo-morpholin-4-yl)-piperidin-1-yl]-ethoxy}-7-methoxy-quinazoline, 4-[(3-chloro-4-fluoro-phenyl)amino]-6-(trans-4-amino-cyclohexan-1-yloxy)-7-methoxy-quinazoline, 4-[(3-chloro-4-fluoro-phenyl)amino]-6-(trans-4-methanesulphonylamino-cyclohexan-1-yloxy)-7-methoxy-quinazoline, 4-[(3-chloro-4-fluoro-phenyl)amino]-6-(tetrahydropyran-3-yloxy)-7-methoxy-quinazoline, 4-[(3- chloro-4-fluoro-phenyl)amino]-6-{1-[(morpholin-4-yl)carbonyl]-piperidin-4-yloxy}-7-methoxy-quinazoline, 4-[(3-chloro-4-fluoro-phenyl)amino]-6-(piperidin-3-yloxy)-7-methoxy-quinazoline, 4-[(3-chloro-4-fluoro-phenyl)amino]-6-[1-(2-acetylamino-ethyl)-piperidin-4-yloxy]-7-methoxy-quinazoline, 4-[(3-chloro-4-fluoro-phenyl)amino]-6-(tetrahydropyran-4-yloxy)-7-ethoxy-quinazoline, 4-[(3-chloro-4-fluoro-phenyl)amino]-6-{trans-4-[(morpholin-4-yl)carbonylamino]cyclohexan-1-yloxy}-7-methoxy-quinazoline, 4-[(3-chloro-4-fluoro-phenyl)amino]-6-{1-[(piperidin-1-yl)carbonyl]-piperidin-4-yloxy}-7-methoxy-quinazoline, 4-[(3-chloro-4-fluoro-phenyl)amino]-6-(cis-4-{N-[(morpholin-4-yl)carbonyl]-N-methyl-amino}-cyclohexan-1-yloxy)-7-methoxy-quinazoline, 4-[(3-chloro-4-fluoro-phenyl)amino]-6-(trans-4-ethanesulphonylamino-cyclohexan-1-yloxy)-7-methoxy-quinazoline, 4-[(3-chloro-4-fluoro-phenyl)amino]-6-(1-methanesulphonyl-piperidin-4-yloxy)-7-(2-methoxy-ethoxy)-quinazoline, 4-[(3-chloro-4-fluoro-phenyl)amino]-6-[1-(2-methoxy-acetyl)-piperidin-4-yloxy]-7-(2-methoxy-ethoxy)-quinazoline, 4-[(3-ethynyl-phenyl)amino]-6-(tetrahydropyran-4-yloxy]-7-methoxy-quinazoline, 4-[(3-chloro-4-fluoro-phenyl)amino]-6-(cis-4-{N-[(piperidin-1-yl)carbonyl]N-methyl-amino}-cyclohexan-1-yloxy)-7-methoxy-quinazoline, 4-[(3-chloro-4-fluoro-phenyl)amino]-6-{cis-4-[(morpholin-4-yl)carbonylamino]-cyclohexan-1-yloxy}-7-methoxy-quinazoline, 4-[(3-chloro-4-fluoro-phenyl)amino]-6-{1-[2-(2-oxopyrrolidin-1-yl)ethyl]piperidin-4-yloxy}-7-methoxy-quinazoline, 4-[(3-ethynyl-phenyl)amino]-6-(1-acetyl-piperidin-4-yloxy)-7-methoxy-quinazoline, 4-[(3-ethynyl-phenyl)amino]-6-(1-methyl-piperidin-4-yloxy)-7-methoxy-quinazoline, 4-[(3-ethynyl-phenyl)amino]-6-(1-methanesulphonyl-piperidin-4-yloxy)-7-methoxy-quinazoline, 4-[(3-chloro-4-fluoro-phenyl)amino]-6-(1-methyl-piperidin-4-yloxy)-7-(2-methoxy-ethoxy)-quinazoline, 4-[(3-ethynyl-phenyl)amino]-6-{1-[(morpholin-4-yl)carbonyl]piperidin-4-yloxy}-7-methoxy-quinazoline, 4-[(3-chloro-4-fluoro-phenyl)amino]-6-{1-[(N-methyl-N-2-methoxyethyl-amino)carbonyl]-piperidin-4-yloxy}-7-methoxy-quinazoline, 4-[(3-chloro-4-fluoro-phenyl)amino]-6-(1-ethyl-piperidin-4-yloxy)-7-methoxy-quinazoline, 4-[(3-chloro-4-fluoro-phenyl)amino]-6-[cis-4-(N-methanesulphonyl-N-methyl-amino)-cyclohexan-1-yloxy]-7-methoxy-quinazoline, 4-[(3-chloro-4-fluoro-phenyl)amino]-6-[cis-4-(N-acetyl-N-methyl-amino)-cyclohexan-1-yloxy]-7-methoxy-quinazoline, 4-[(3-chloro-4-fluoro-phenyl)amino]-6-(trans-4-methylamino-cyclohexan-1-yloxy)-7-methoxy-quinazoline, 4-[(3-chloro-4-fluoro-phenyl)amino]-6-[trans-4-(N-methanesulphonyl-N-methyl-amino)-cyclohexan-1-yloxy]-7-methoxy-quinazoline, 4-[(3-chloro-4-fluoro-phenyl)amino]-6-(trans-4-dimethylamino-cyclohexan-1-yloxy)-7-methoxy-quinazoline, 4-[(3-chloro-4-fluoro-phenyl)amino]-6-(trans-4-{N-[(morpholin-4-yl)carbonyl]N-methyl-amino}-cyclohexan-1-yloxy)-7-methoxy-quinazoline, 4-[(3-chloro-4-fluoro-phenyl)amino]-6-[2-(2,2-dimethyl-6-oxo-morpholin-4-yl)-ethoxy]-7-[(S)-(tetrahydrofuran-2-yl)methoxy]-quinazoline, 4-[(3-chloro-4-fluoro-phenyl)amino]-6-(1-methanesulphonyl-piperidin-4-yloxy)-7-methoxy-quinazoline, 4-[(3-chloro-4-fluoro-phenyl)amino]-6-(1-cyano-piperidin-4-yloxy)-7-methoxy-quinazoline, and 4-[(3-chloro-4-fluoro-phenyl)amino]-6-{1-[(2-methoxyethyl)carbonyl]-piperidin-4-yloxy}-7-methoxy-quinazoline, optionally in the form of the racemates, enantiomers or diastereomers thereof, optionally in the form of the pharmacologically acceptable acid addition salts thereof, the solvates and/or hydrates thereof.

By acid addition salts with pharmacologically acceptable acids which the compounds may be capable of forming are meant, for example, salts selected from among the hydrochloride, hydrobromide, hydriodide, hydrosulphate, hydrophosphate, hydromethanesulphonate, hydronitrate, hydromaleate, hydroacetate, hydrobenzoate, hydrocitrate, hydrofumarate, hydrotartrate, hydroxalate, hydrosuccinate, hydrobenzoate and hydro-p-toluenesulphonate, preferably the hydrochloride, hydrobromide, hydrosulphate, hydrophosphate, hydrofumarate and hydromethanesulphonate.

Examples of antiallergics are: disodium cromoglycate, nedocromil.

Examples of ergot alkaloids are: dihydroergotamine, ergotamine.

Examples of substances suitable for inhalation include medicaments containing the above-mentioned active substances, and the salts and esters thereof and combinations of these active substances, salts and esters.

Preferably the plastics from which individual parts of the inhaler are produced are polymers, thermoplastic polycondensates, polyadducts, modified natural substances or rubbers or mixtures of these plastics.

Particularly preferred in this case are polyolefins, vinyl chloride polymers, styrene polymers, polyacetals, polyamides, thermoplastic polyesters and polyarylethers or mixtures of these plastics. Examples of these plastics are polyethylene, polyvinyl chloride, polyoxymethylene, polyacetal, acrylonitrile/butadiene/styrene (ABS), acrylonitrile/styrene/acrylic ester (ASA), polyamides, polycarbonate, poly(ethyleneterephthalate), poly(butyleneterephthalate) or poly(phenylene ether). Plastics of this kind may be obtained for example from the company Ensinger in Nufringen, Germany.

According to one feature the cover comprises an exit opening and an entry opening, which are arranged at a spacing from each other in the region of the mouthpiece, while at least the exit opening is arranged in the region of the dish-shaped cavity that is to be emptied. Accordingly, the flow channel is configured so that at least some of the discharge flow produced on inhaling flows out over the medicament contained in the cavity and carries it along. The break-up and dispersion of the medicament can be influenced by an internal configuration of the cavity and/or the exit or entry opening and/or the mouthpiece.

Expediently, the mouthpiece which is open at both ends has a cross-sectional constriction between the in particular slot-shaped exit opening and the entry opening. Starting from an open entry end remote from the user of the inhaler, the air sucked in during inhalation flows through both the cross-sectional constriction and the entry opening into the cavity and, laden with medicament, flows through the exit opening to the exit end of the mouthpiece. The cross-sectional constriction improves the break-up and dispersion of the medicament in the mouthpiece by means of turbulence.

Preferably, the mouthpiece is held, more particularly releasably, in a defined position in a receptacle in the form of a T-shaped groove in the cover. The T-groove-shaped receptacle assists with the mounting of the mouthpiece or its attachment to the cover during the manufacture of the inhaler. If the mouthpiece is releasably attached to the cover it can be removed from the magazine for cleaning. It is also possible to replace only the magazine if necessary and to continue using the mouthpiece.

According to a further feature the housing comprises a base to which the cover is non-removably attached in sealed manner. If both the cover and the base are made of a plastics material, they may be joined together by welding, for example. Naturally, the carrier is protected by being held between the cover and the base.

Preferably, the housing has a circular cross-section and provides a latching rotatable mounting for the disc-shaped carrier, while an actuating device for stepwise rotation of the carrier is associated with the housing and the carrier so as to move a cavity that is to be emptied into the flow channel with the mouthpiece. Using the actuating device the user can move the carrier so that a cavity filled with the medicament moves into the flow channel, i.e. underneath the exit opening at the cover end, and assumes a defined position therein. Thus the inhaler is easy and reliable to operate.

According to a further feature, two disc-shaped carriers are rotatably mounted in locking manner in the housing, so as to be rotatably located directly above one another, while the carrier associated with the mouthpiece comprises an exit opening and an entry opening which correspond to the outlet opening and inlet opening of the cover. In this way a plurality of doses of a medicament to be administered can be stored in a magazine of compact construction. The medicament from the carrier on the base side passes through the exit opening in the carrier on the mouthpiece side and the exit opening in the cover into the mouthpiece. At the same time, the air sucked in is guided through the entry opening of the cover and the inlet opening of the carrier on the mouthpiece side to the cavity, the two carriers naturally being located with their facing end faces directly against one another so as to prevent loss of flow and loss of medicament.

In order to provide a mount of simple construction, the carrier facing the mouthpiece comprises a circumferential flange with an external diameter greater than that of the carriers, in which on the one hand the carrier on the base side is mounted with its end face comprising the cavities and on the other hand is supported in the housing. It goes without saying that an additional spindle may pass through the entire housing of the magazine with its carriers to ensure accurate guidance.

Advantageously, the actuating device comprises an actuating element that is mounted in the base so as to be movable along a circular path, this actuating element engaging via a spring arm in equidistant recesses in the carrier on the base side, and the two carriers have tappets that move into mutual abutment when the carrier on the base side is rotated by one revolution out of a starting position. This provides an actuating device of simple construction for reliably rotating the two carriers in the housing.

In order to achieve precise positioning, for stepwise rotation of the two carriers at least one spring arm cooperating with the circumference of the pot-shaped cover is expediently associated with each carrier. In particular, two diametrically opposed spring arms are provided on each carrier, while the carriers may for example be manufactured in one piece with the spring arms by an injection moulding process.

For further improving the handling of the inhaler and for ensuring the efficacy of the medicament, a desiccant and/or a, more particularly, digital moisture indicator is or are provided inside the housing. Of course, the desiccant, which has no negative effects on the medicament stored in the magazine of the inhaler, can be accommodated in a special chamber. The moisture indicator provides information as to the relative humidity within the housing, which is visually apparent to the user, by means of which it is possible to determine whether or not the medicament can be used, for example. A digital moisture indicator may comprise changing colours, particularly green and red, or a written warning notice.

In order to obtain the most uniform possible distribution of the pharmaceutical powder formulation, the mouthpiece is fitted with a dispersing unit.

Expediently, each cavity is designed to hold about 50 mg of the medicament and the magazine preferably comprises 30 cavities. The cavities are distributed equidistantly over the circumference of the carrier, including a blank position which comprises the outlet opening and the inlet opening on the carrier on the cover side, each carrier having 15 cavities. Theoretically, any other number of cavities is also possible, for example four, six, eight, ten, twelve, 16, 20, 24 or 32.

For monitoring the contents of different cavities in the magazine of the inhaler, the housing is constructed to be at least partly transparent, to enable a visual check to be made through this transparent section as to whether one or more cavities have already been emptied or are still full. For example, the transparent section is arranged such that it is always possible to see into the particular cavity that will be accessed next through the mouthpiece, i.e. the one in front of a dispensing or inhaling position, viewed in the direction of rotation of the carriers.

To protect the medicament in the cavities of the carriers of the magazine from moisture over relatively long periods, a removable moistureproof outer wrapper for the inhaler and/or the magazine is provided.

It will be understood that the features mentioned above and still to be explained hereinafter may be used not only in the particular combination stated but also in other combinations. The scope of the invention is defined only by the claims.

The invention is hereinafter explained in more detail by means of an embodiment by way of example with reference to the accompanying drawings, wherein:

FIG. 1 is a plan view of an inhaler according to the invention,

FIG. 2 is a side view of the inhaler according to FIG. 1,

FIG. 3 is a plan view of a mouthpiece of the inhaler according to FIG. 1,

FIG. 4 is a sectional view of the mouthpiece along the line IV-IV in FIG. 3,

FIG. 5 is a plan view of a restrictor for the mouthpiece according to FIG. 3,

FIG. 6 is a plan view of a cover of the inhaler according to FIG. 1,

FIG. 7 is a sectional view of the cover on the line VII-VII in FIG. 6,

FIG. 8 is a plan view of a base of the inhaler according to FIG. 1,

Figure 9:
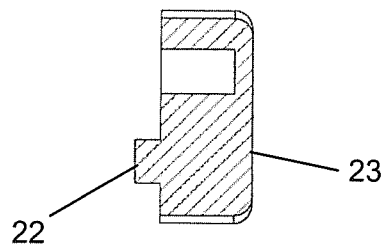
FIG. 9 is a sectional view of an actuator of the inhaler according to FIG. 1.
Figure 10:
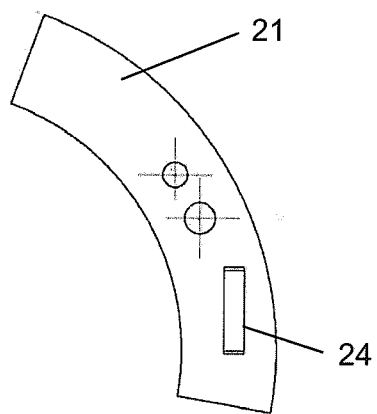
Figure 11:
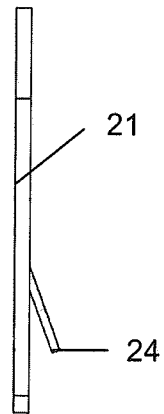

FIG. 10 is a plan view of an actuating element of the inhaler according to FIG. 1, FIG. 11 is a side view of the actuating element according to FIG. 10, FIG. 12 is a plan view of a carrier of the inhaler according to FIG. 1, FIG. 13 is a sectional view of the carrier on the line XIII-XIII according to FIG. 12, FIG. 14 is a plan view of another carrier of the inhaler according to FIG. 1 and FIG. 15 is a sectional view of the carrier on the line XV-XV in FIG. 14.

The inhaler 1 is configured as a so-called multi-dose powder inhaler for administering a powdered medicament in the form of an inhalable substance, substance formulation or mixture, and comprises a mouthpiece 2 that is connected to a housing 3 of a magazine for holding a plurality of doses of the medicament. The housing 3 consists essentially of a cover 4 and a base 5 fixedly attached thereto, the cover 4 having two legs 6 to form a receptacle 7 in the form of a T-shaped groove for the mouthpiece 2. Between the two legs 6, a slot-shaped exit opening 8 and an entry opening 9 for an airflow are provided in the cover 4 at a spacing from one another. In the region of the exit 8 and entry opening 9 a raised sealing surface 10 on which the mouthpiece 2 partially rests is formed on the cover 4. In the centre of the cover 4 is a bore 11 for accommodating a spindle passing through the housing 3. The cover 3 is substantially pot-shaped while an attachment 13 for centering the base 5 and equidistantly distributed indentations 14 are formed on the circumferential wall 12.

The mouthpiece 2 has a channel 15 extending through its longitudinal axis, in which is inserted a restrictor 16 that reduces the cross-section of the channel 15. Perpendicularly to the longitudinal axis of the mouthpiece 2 a recess 17 is formed in the mouthpiece 2, into which the restrictor 16 is inserted such that it is located in the position of the mouthpiece 2 mounted on the cover 4 between the exit 8 and entry opening 9 of the cover 4 and forms a flow channel through a depression 18 in the restrictor 16. The part of the mouthpiece 2 that is to be secured has legs 19 on both sides for insertion in the T-groove-shaped receptacle 7 in the cover 4.

The base 5 is provided with an opening 20 in the shape of a segment of a circle, through which an actuator 23 connected by bolts 22 to an equally segment-shaped actuating element 21 projects, the actuating element 21 comprising a spring arm 24 projecting into the housing 3. Moreover, a chamber 25 for a desiccant is formed on the base 5.

Rotatably mounted in the housing 3 of circular cross-section are two circular carriers 26, 27 arranged immediately above one another, on which two diametrically opposed spring arms 28 are arranged which cooperate for stepwise positioning of the carriers 26, 27 with the circumferential indentations 14 of the pot-shaped cover 4. Moreover, each carrier 26, 27 comprises a tappet 29 which can cooperate with the tappet 29 of the other carrier 26, 27 in each case.

The carrier 27 on the base side comprises, on its end face 30 facing the base 5, equidistantly distributed recesses in which the spring arm 24 of the actuating element 21 engages. Moreover, including a blank position 31, dish-shaped cavities 32 for holding the medicament are uniformly distributed around the circumference of the carrier 27.

The cavities 32 uniformly distributed around the circumference of the carrier 26 are also formed on the end face 33 facing the cover 4, in the carrier 26 on the cover side, while in one position 34, instead of a cavity 32, an outlet opening 35 and an inlet opening 36 are provided which correspond to the exit opening 8 and the entry opening 9 of the cover 4, the outlet opening 35 and the exit opening 8 each being slot-shaped and the inlet opening 36 and the entry opening 9 each being cylindrical in shape. Furthermore, the carrier 26 facing the mouthpiece 2 has a circumferential flange 37 that is larger in its external diameter than the carriers 26, 27, in which on the one hand the carrier 27 on the base side is mounted with its end face 38 comprising the cavities 32, and on the other hand is supported in the cover 4 of the housing 3.

In an initial state of the inhaler 1 in which all the cavities 32 are filled with the medicament, the outlet opening 35 and the inlet opening 36 of the carrier 26 on the cover side are in a position that is flush with the exit opening 8 and the entry opening 9 of the cover 4, and the blank position 31 of the carrier 27 on the base side is aligned with the exit opening 8 and the entry opening 9 underneath the position 34 of the carrier 26 on the cover side. As the cover 4 rests directly on the associated end face 33 of the carrier 26 on the cover side and the carrier 26 on the cover side rests directly at its end face on the carrier 27 on the base side, no medicament is able to escape from the cavities 32.

In order to use the inhaler, the actuating element 21 is moved along with the actuator 23, the spring arm 24 of the actuating element 21 engaging in one of the recesses of the carrier 27 on the base side and rotating said carrier 27 until the spring arms 28 latch in the corresponding indentations 14 in the cover 4, so as to position the cavity 32 that is associated with the rotational position under the outlet opening 35 and the inlet opening 36 of the carrier 26 on the cover side. The user sucks air through the channel 15 of the mouthpiece 2, which is passed through both the restrictor 16 and the entry opening 8 of the cover 4 and the inlet opening 35 of the carrier 26 on the mouthpiece side to the cavity 32 that is to be emptied, in order to convey the medicament through the outlet opening 35 of the carrier 26 on the cover side, the exit opening 8 of the cover 4 and the channel 15 of the mouthpiece 2 to the user. In this position in which the emptied cavity 32 is aligned underneath the outlet opening 35 and the inlet opening 36 of the carrier 26 on the cover side, the inhaler 1 can be transported. Moving the actuator 24 back and forth rotates the carrier 27 on the base side in order to position the next cavity 32 under the outlet opening 35 and the inlet opening 36 of the carrier 26 on the cover side. Once all the cavities 32 of the carrier 27 on the base side have been emptied, the two tappets 29 move into mutual engagement and a rotary movement of the carrier 27 on the base side is accompanied by a rotary movement of the carrier 26 on the cover side, in order to arrange the cavities 32 therein underneath the exit opening 8 and the entry opening 9 of the cover 4 for emptying, while when the two carriers 26, 27 are rotated for accurately positioning the wells 32 all the spring arms 28 are operational.

| List of reference numerals | |
|---|---|
| 1. | inhaler |
| 2. | mouthpiece |
| 3. | housing |
| 4. | cover |
| 5. | base |
| 6. | leg of 7 |
| 7. | receptacle |
| 8. | exit opening |
| 9. | entry opening |
| 10. | sealing surface |
| 11. | bore |
| 12. | wall of 4 |
| 13. | attachment |
| 14. | indentation |
| 15. | channel |
| 16. | restrictor |
| 17. | recess |
| 18. | depression of 16 |
| 19. | leg of 2 |
| 20. | opening |
| 21. | actuating element |
| 22. | bolt |
| 23. | actuator |
| 24. | spring arm |
| 25. | chamber |
| 26. | carrier |
| 27. | carrier |
| 28. | spring arm of 26, 27 |
| 29. | tappet |
| 30. | end face of 27 |
| 31. | blank position |
| 32. | cavity |
| 33. | end face of 26 |
| 34. | position |
| 35. | outlet opening |
| 36. | inlet opening |
| 37. | flange |
| 38. | end face of 27 |

The invention claimed is:

1. An inhaler for administering a medicament in a form of an inhalable formulation, comprising:
   a housing (3) having a base (5) and a cover (4) defining an internal volume and a longitudinal axis, where the cover (4) includes an entry opening (9) and an exit opening (8) in fluid communication with the internal volume;
   a mouthpiece (2) coupled to the cover (4) and including a longitudinally extending channel (15) in fluid communication with each of the entry opening (9) and the exit opening (8) of the cover (4);
   a first carrier (27) having a plurality of unsealed cavities (32), each one of the plurality of unsealed cavities (32) containing a dose of the medicament, and being disposed within the internal volume of the housing (3) towards the base (5); and
   a second carrier (26) having a plurality of unsealed cavities (32), each one of the plurality of unsealed cavities (32) containing a dose of the medicament, and being disposed over the first carrier (27) within the internal volume of the housing (3) towards the cover (4) along the longitudinal axis, where the second carrier (26) includes an inlet opening (36) and an outlet opening (35), each extending through the second carrier (26), wherein:
   the inlet opening (36) and the outlet opening (35) are movable with respect to respective ones of the plurality of unsealed cavities (32) of the first carrier (27), such that the inlet opening (36) and the outlet opening (35) operate to provide a fluidic path through the inlet opening (26) of the second carrier (26) and into a respective one of the plurality of unsealed cavities (32) of the first carrier (27), and out of the respective ones of the plurality of unsealed cavities (32) of the first carrier (27) and through the outlet opening (37) of the second carrier (26), and
   the entry opening (9) and the exit opening (8) of the cover are in fluidic communication with the inlet opening (36) and the outlet opening (35), respectively, of the first carrier (27), such that the fluidic path carries the medicament from the respective one of the plurality of unsealed cavities (32) of the first carrier (27) into the longitudinally extending channel (15) for delivery to a user.

2. The inhaler according to claim 1, wherein the plurality of unsealed cavities (32) are cup-shaped and the opening (8) and the entry opening (9) in the cover (4) are arranged at a spacing from each other adjacent to the mouthpiece (2), while at least the exit opening (8) is arranged in proximity to the respective ones of the plurality of unsealed cavities (32) that is to be emptied.

3. The inhaler according to claim 1, wherein the channel (15) of the mouthpiece (2) includes: (i) a first end open to an ambient environment and in fluidic communication with the entry opening (9) of the cover (4), (ii) a second end open to the ambient environment and in fluidic communication with the exit opening (8) of the cover (4), and (iii) a cross-sectional constriction in a flow path between the entry opening (9) and the exit opening (8).

4. The inhaler according to claim 1, further comprising a receptacle (7) operating to releasably hold the mouthpiece (2) in position on the cover (4).

5. The inhaler according to claim 1, wherein the base (5) is non-removably attached in a sealed manner to the cover (4).

6. The inhaler according to claim 1, wherein:
   the first carrier (27) and second carrier (26) are each disc shaped and the plurality of unsealed cavities (32) are disposed circumferentially at respective intervals around each said first carrier (27) and said second carrier (26),
   the housing (3) has a circular cross-section and provides a latching rotatable mounting for the disc-shaped first carrier (27) and second carrier (26), and
   the inhaler further comprises an actuating device for independent, stepwise rotation of the first carrier (27) and second carrier (26) such that the inlet opening (36) and the outlet opening (37) are stepwise movable with respect to each of the plurality of unsealed cavities (32) of the first carrier (27) in order to provide respective stepwise fluidic paths from each of the plurality of unsealed cavities (32) of the first carrier (27) into the longitudinally extending channel (15) of the mouthpiece (2) for delivery to the user.

7. The inhaler according to claim 1, wherein the first carrier (27) and second carrier (26) are rotatably mounted in locking manner in the housing (3), so as to be rotatably located directly above one another.

8. The inhaler according to claim 7, wherein:
   the second carrier (26) includes a circumferential flange (37) with an external diameter greater than that of the first carrier (27), and
   the first carrier (27) is mounted with a face (38) comprising the plurality of unsealed cavities (32) adjacent to the second carrier (26) within the flange (37) and is supported on an opposite side of the face (38) within the housing (3).

9. The inhaler according to claim 6, wherein:
   the actuating device comprises an actuating element (21) that is mounted in the base (5) so as to be movable along a circular path, the actuating element (21) engaging via a spring arm (24) in equidistant recesses in the first carrier (27), and
   the first carrier (27) and second carrier (26) each include at least one tappet (29) that move into mutual abutment when the first carrier (27) has rotated through one revolution from a starting position.

10. The inhaler according to claim 6, wherein for stepwise rotation of the first carrier (27) and second carrier (26), at least one spring arm (28) cooperating with a circumference of the cover (4), which is pot-shaped, is associated with each of the first carrier (27) and second carrier (26).

11. The inhaler according to claim 1, wherein at least one of a desiccant and a digital moisture indicator is provided inside the housing (3).

12. The inhaler according to claim 1, wherein the mouthpiece (2) is fitted with a dispersing unit.

13. The inhaler according to claim 1, wherein each one of the plurality of unsealed cavities (32) is designed to hold 50 mg of a pharmaceutical powdered formulation and the housing (3) preferably comprises thirty cavities (32).

14. The inhaler according to claim 1, wherein the housing (3) is constructed to be at least partly transparent.

15. The inhaler according to claim 1, further comprising at least one of a removable moisture-proof outer wrapper and an outer wrapper for the housing (3).

16. Inhaler according to claim 6, wherein:
   operation of the actuating device in a back and forth manner operates to rotate the first carrier (27) by one of the independent, stepwise rotations with respect to the second carrier (26) such that the inlet opening (36) and the outlet opening (37) move into fluidic communication with a next one of the plurality of unsealed cavities (32) of the first carrier (27), the first carrier (27) and second carrier (26) each include at least one tappet (29) that move into mutual abutment when the first carrier (27) has rotated through one revolution from a starting position, and when the at least one tappet (29) of the first carrier (27) and second carrier (26) have moved into abutment, further operation of the actuating device in the back and forth manner continues to rotate the first carrier (27) along with corresponding rotary movement of the second carrier (26), such that the entry opening (9) and the exit opening (8) of the cover (4) are in stepwise, fluidic communication with respective ones of the plurality of unsealed cavities (32) of the second carrier (26), such that respective stepwise fluidic paths carry the medicament from the respective ones of the plurality of unsealed cavities (32) of the second carrier (26) into the longitudinally extending channel (15) for delivery to the user.

* * * * *